(12) United States Patent
King

(10) Patent No.: US 8,439,030 B2
(45) Date of Patent: May 14, 2013

(54) NEBULIZER DEVICE

(76) Inventor: Russell Wayne King, Sierra Madre, CA (US)

(*) Notice: Subject to any disclaimer, the term of this patent is extended or adjusted under 35 U.S.C. 154(b) by 738 days.

(21) Appl. No.: 12/590,571

(22) Filed: Nov. 11, 2009

(65) Prior Publication Data

US 2011/0108022 A1   May 12, 2011

(51) Int. Cl.
*A61M 11/00*   (2006.01)
(52) U.S. Cl.
USPC ............. 128/200.18; 128/200.21; 128/200.14
(58) Field of Classification Search ............. 128/200.14, 128/200.18, 200.24, 203.15, 205.24, 897, 128/203.28, 203.12, 200.21, 207.12, 911, 128/207.14, 205.13, 204.18, 200.25
See application file for complete search history.

(56) References Cited

U.S. PATENT DOCUMENTS

| | | | | |
|---|---|---|---|---|
| 4,529,003 A | * | 7/1985 | Iannuzzelli et al. | 137/493.8 |
| 5,301,663 A | * | 4/1994 | Small, Jr. | 128/200.18 |
| 5,752,502 A | * | 5/1998 | King | 128/200.18 |
| 6,679,250 B2 | * | 1/2004 | Walker et al. | 128/200.21 |
| 7,350,520 B1 | * | 4/2008 | Richard-Bey | 128/200.21 |
| 2006/0231090 A1 | * | 10/2006 | King | 128/200.14 |

* cited by examiner

*Primary Examiner* — Steven Douglas
(74) *Attorney, Agent, or Firm* — James E. Brunton

(57) ABSTRACT

An improved tee type nebulizer unit for medicinal use that delivers a mist of properly sized aerosol particles of medicament to the patient. A uniquely configured air flow baffle assembly, which is strategically positioned within the tee of the nebulizer unit, markedly increases the rate of liquid-to-aerosol conversion compared to prior art tee type nebulizer units. More particularly, due to the positioning and sizing of the air channeling pathways within the air flow baffle assembly, an increase in rate of aerosol mist production by factors of 200%-300% is realized.

5 Claims, 5 Drawing Sheets

FIG. I
PRIOR ART

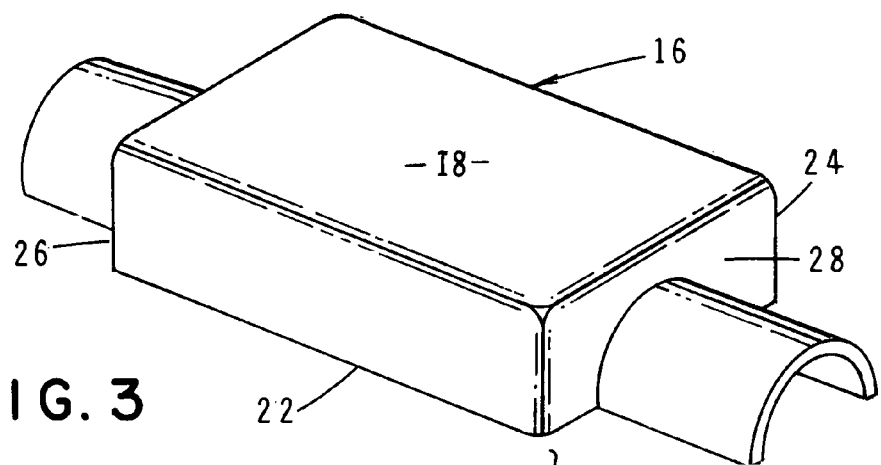
FIG. 3
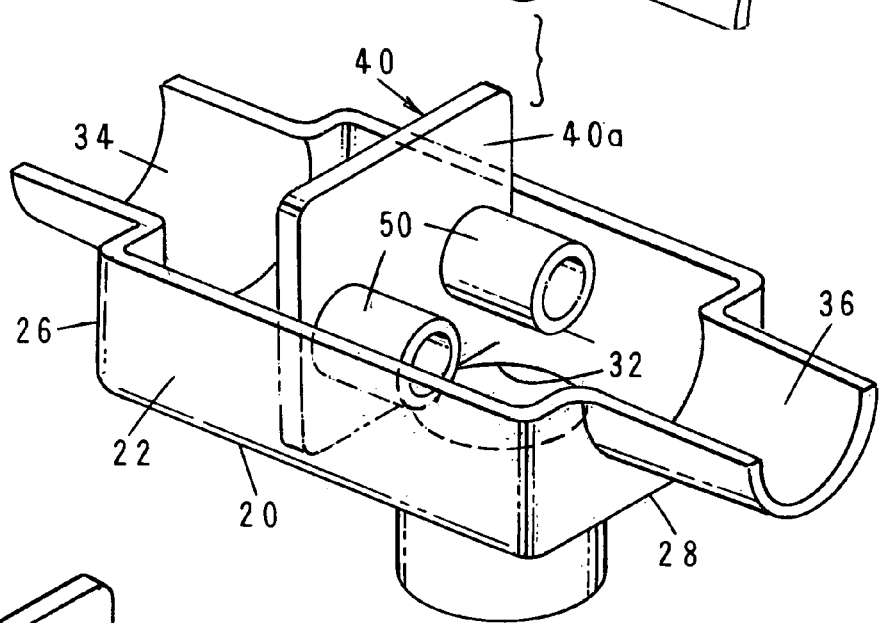
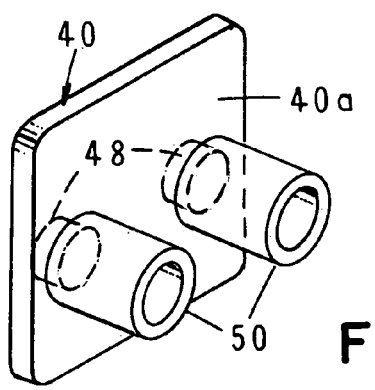
FIG. 4

US 8,439,030 B2

NEBULIZER DEVICE

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates generally to inhalation devices. More particularly, the invention concerns a tee type nebulizer device for medicinal use that delivers an aerosol mist of properly sized particles of medicament to the patient at a very rapid rate.

2. Discussion of the Prior Art

Delivery of medication to a patient's lungs by means of jet nebulization has been an accepted procedure in the medical community for many years. Predominantly the device used has been a simple 3-way medical tee with one end interfaced to the patient, the other end open to room air, and the nebulizer component attached to an intermediate third port. Millions of these devices are produced and used annually.

Published data (Respiratory Care, Vol. 38, No. 38, Aug. 93; and Advance for Respiratory Care Practitioners Aug. 9, 1993) indicate that the most limiting factor in the use of aerosolized medication is the inefficient mist production by currently available commercial nebulizer systems. Research has shown that most state-of-the-art commercial units deliver less than 10% of the original dose of medication to the patient's respiratory tract. (Respiratory Care, Vol. 38, #8, August 1993; and AARC Times, June 1993.)

Jet nebulization is a process whereby a flow of gas (typically air or oxygen) through a very small orifice creates a partial vacuum in the fluid passageways of the device. This reduction in pressure is sufficient to create a Venturi effect, pulling liquid from a reservoir to mix into the gas stream. This liquid is subsequently changed within the device into aerosol particles.

Physical constraints in the design of jet nebulizers for medical use are such that the conversion rate of Liquid-to-aerosol is limited to a maximum of approximately 0.35 ml per minute of operation. This is a determining factor that determines the lengthy time (usually in excess of ten minutes) required for delivery of a clinically effective treatment when using any typical present day tee type nebulizer device. Not only is this wasteful, but because of the excessive time required for delivery of a clinically effective treatment, this type device is not user friendly. It is this problem that the present invention seeks to solve by improving the nebulizer design to include special baffling within the tee adapter of the device.

SUMMARY OF THE INVENTION

It is an object of the present invention to provide an improved tee type nebulizer device that includes a strategically positioned air flow baffle assembly that markedly increases the rate of liquid-to-aerosol conversion. More particularly, due to the positioning and sizing of the air channeling pathways within the air flow baffle assembly, bench studies have shown an increase in rate of aerosol mist production by factors of 200%-300%.

Another object of the invention is to provide a device of the aforementioned character that is capable of aerosolizing liquid medicaments at a rate of up to 1 milliliter (ml) per minute.

Another object of the invention is to provide a device of the character described that will aerosolize and deliver a clinically viable patient dose (0.2-0.3 mg Albuterol) from a standard 2.5 mg/3 ml nebulizer charge in 3 minutes or less.

Another object of the invention is to provide a nebulizer device that is physically small in size for convenience of packaging, storage, dispensing and operation.

Yet another object of the invention is to provide a medical aerosol device that is operable with either air or oxygen at flow rates between about 5 and about 8 liters per minute (LPM).

Yet another object is to provide a tee/nebulizer device that, can be used in conjunction with various patient interfaces such as a mouthpiece, face mask, or special nasal mask.

Another object of the current invention is to provide the capability of readily attaching a commercial filter when needed for exit gas purification prior to atmospheric release.

BRIEF DESCRIPTION OF THE DRAWINGS

FIG. 3 is an enlarged generally perspective exploded view of the body portion of the device shown in FIG. 2 illustrating the positioning of the baffle assembly of the device within the body portion.

FIG. 4 is a generally perspective view of the baffle assembly shown in FIG. 3.

DETAILED DESCRIPTION OF THE INVENTION

Figure 1:
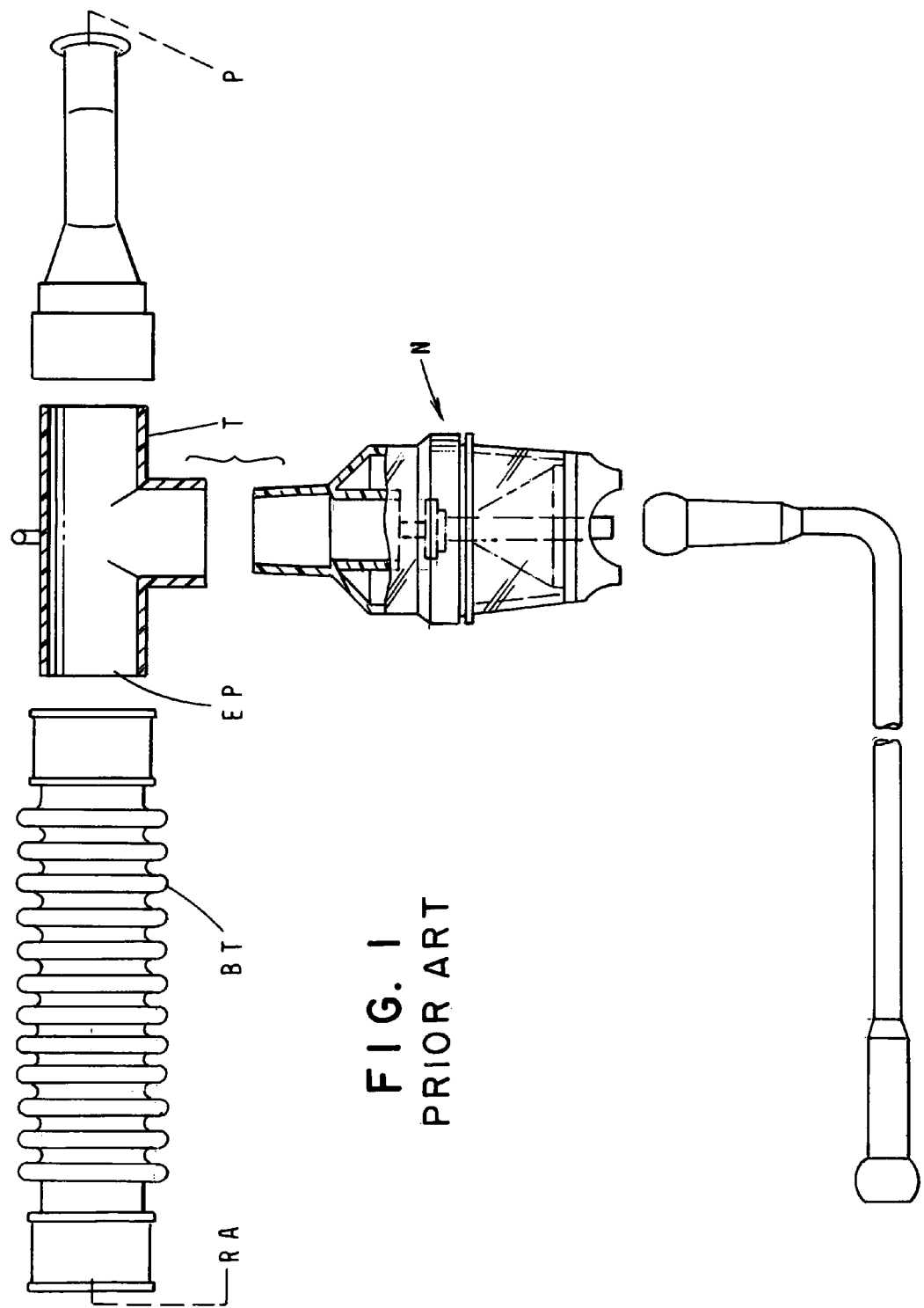
FIG. 1 is a side elevational, exploded view, partly in cross section of a typical prior art tee type nebulizer device.

Referring to the drawings and particularly to FIG. 1 a typical prior art tee type nebulizer device is there shown. As is apparent from a study of FIG. 1 the medical tee "T" serves only as an inter-connecting pathway for gas flow between the nebulizer "N", the patient "P" (at the mouthpiece), and room air "RA" via an elongated breathing tube "BT" that is attached to the exit port "EP" of the medical tee component. The function of the breathing tubing is to limitedly increase device efficiency.

Figure 2:
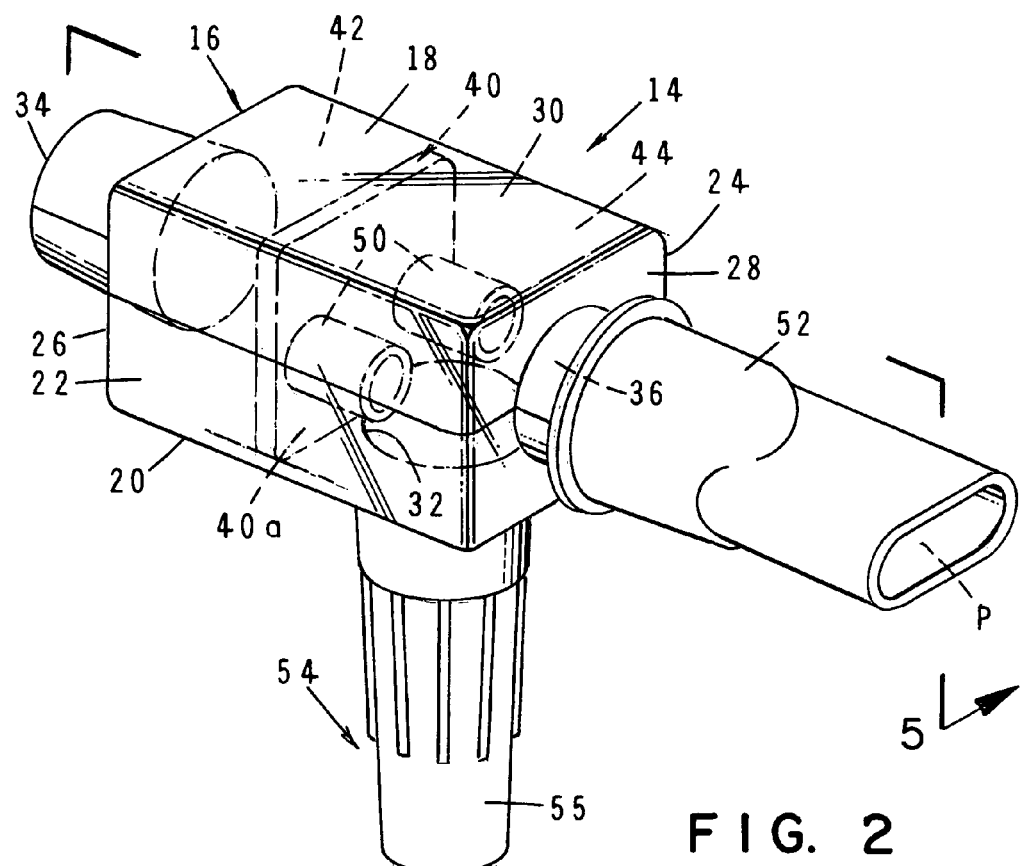
FIG. 2 is a generally perspective view of one form of the improved tee type nebulizer device of the present invention.

Turning now to FIG. 2 of the drawings, one form of the improved tee type nebulizer unit of the present invention for delivering a multiplicity of particles of aerosolized medication to a patient is there shown and generally designated by the numeral 14. Nebulizer unit 14 here comprises a nebulizer housing 16 having interconnected top, bottom, side and end walls 18, 20, 22, 24, 26 and 28 respectively that cooperate to define an internal chamber 30. Bottom wall 20 has a nebulizer port 32, end wall 26 has an inlet port 34 and end wall 28 has a particle outlet port 36 in communication with the patient "P".

Connected to and spanning the top, bottom and side walls 18, 20, 22 and 24 is an airflow baffle assembly 40. Airflow baffle assembly 40 (FIG. 4), which forms an extremely important feature of the invention, is strategically located between nebulizer port 32 and inlet port 34 and functions to divide internal chamber 30 into first and second sub-chambers 42 and 44 respectively (FIG. 2). Airflow baffle assembly includes a baffle plate 40a having a pair of transversely spaced apart openings 48 formed therein (FIG. 4) and a pair of transversely spaced apart tubular flow directors 50 extending into second sub-chamber 44. As illustrated in FIG. 2, tubular flow director 50 provides fluid communication between the first and second sub-chambers.

Connected to particle outlet port 36 is a conventional patient mouthpiece 52 and connected to nebulizer port 32 is a nebulizer assembly 54. Nebulizer assembly 54, which also forms an extremely important aspect of the invention, is in communication with second sub-chamber 44 and functions to convert aerosolizable liquid medicament into an aerosolized medication and to then introduce the aerosolized medication into the second sub-chamber. Nebulizer assembly 54 is operable with air and oxygen at flow rates between about 5 and about 8 liters per minute and when functioning in tandem with assembly 14, aerosolizes liquid medicaments at a rate of up to 1 milliliter (ml) per minute and uniquely will aerosolize and deliver to the patient a clinically viable patient dose of 0.2-0.3 mg of Albuterol from a standard 2.5 mg/3 ml nebulizer charge in less than 3 minutes.

Figure 5:
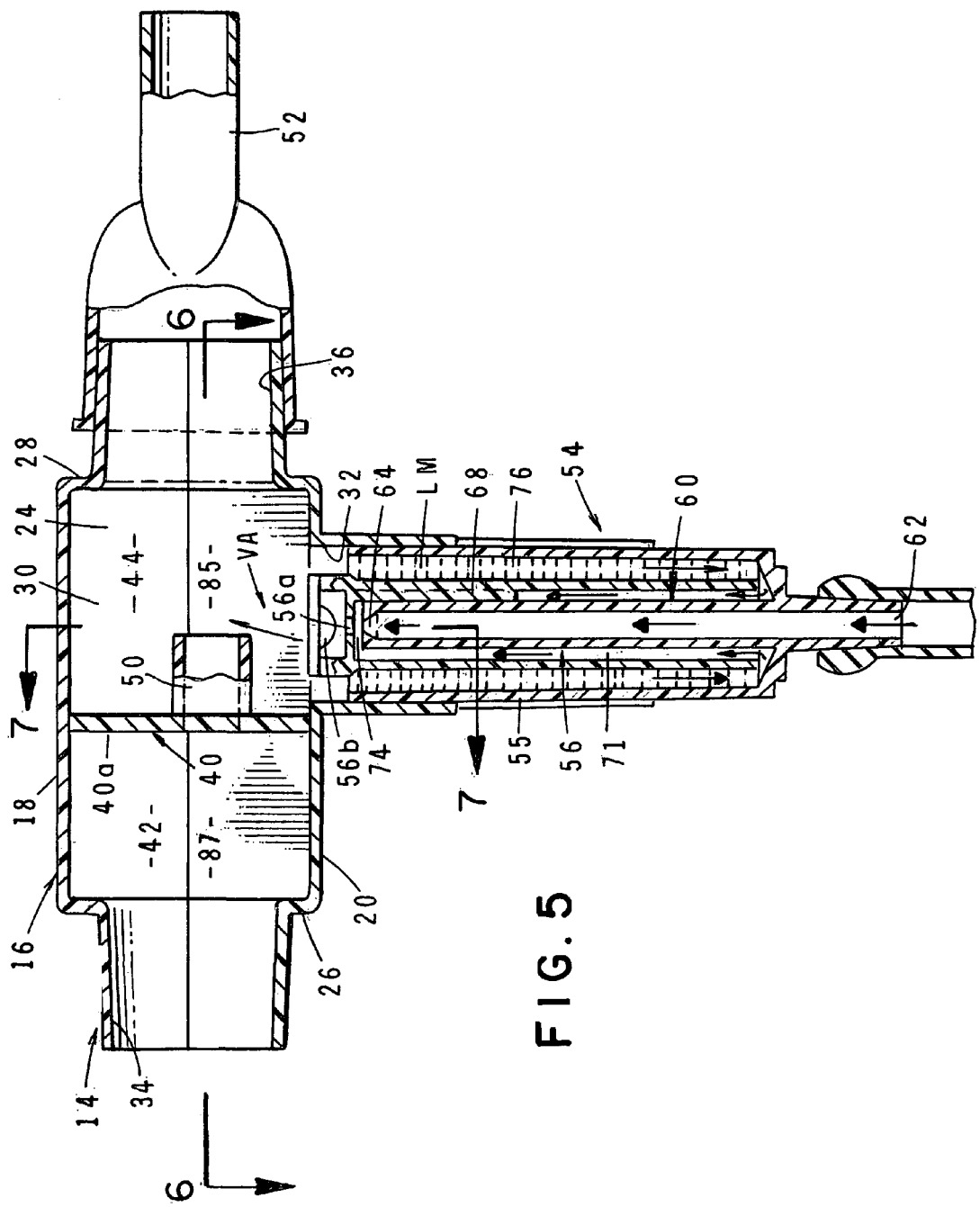
FIG. 5 is an enlarged cross-sectional view taken along lines 5-5 of FIG. 2.
Figure 6:
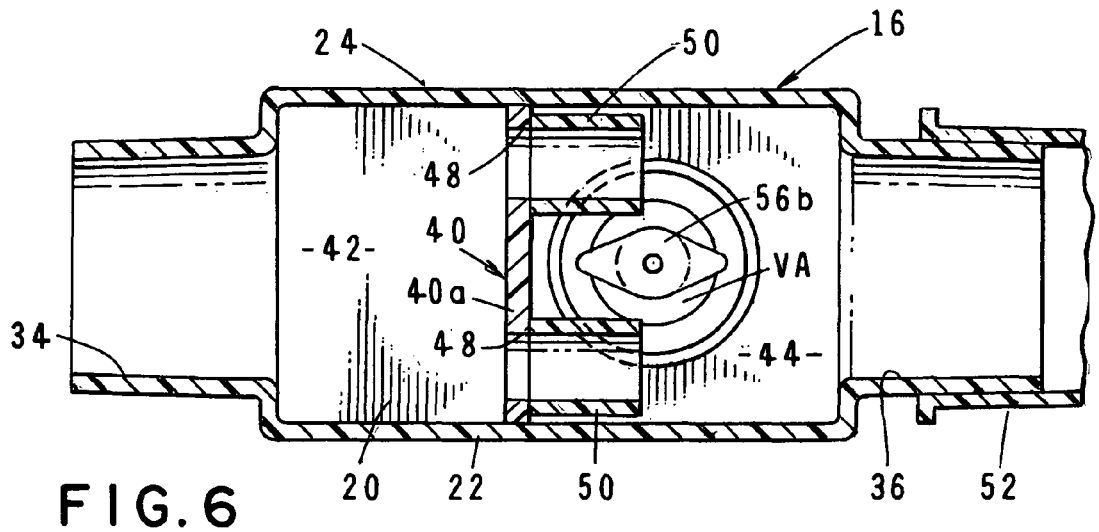
FIG. 6 is a cross-sectional view taken along lines 6-6 of FIG. 5.
Figure 7:
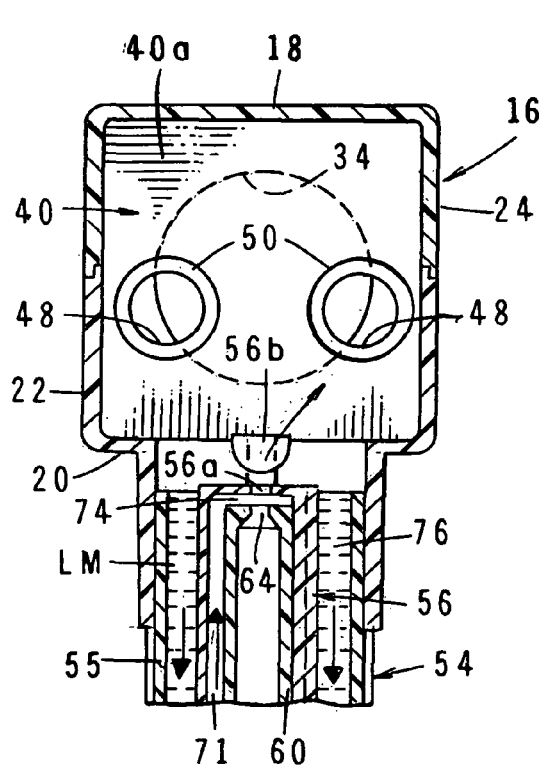
FIG. 7 is a cross-sectional view taken along lines 7-7 of FIG. 5.
Figure 8:
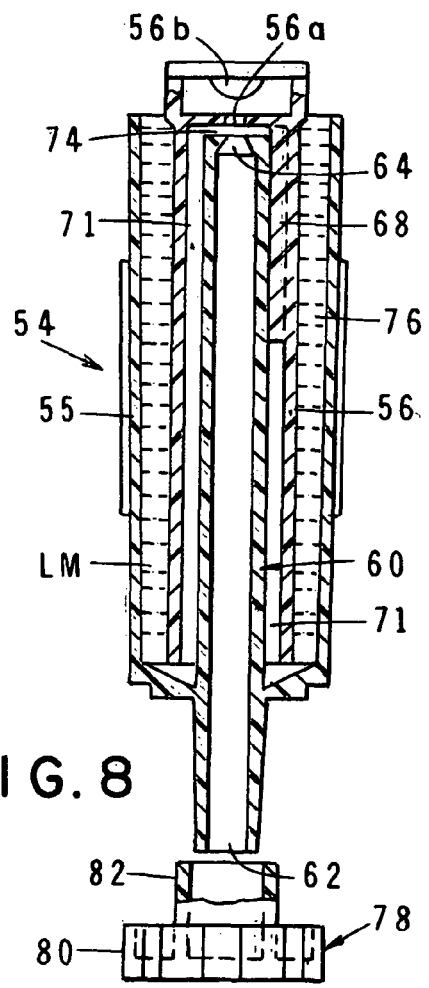
FIG. 8 is an enlarged cross-sectional view of the nebulizer portion of the device along with the stand therefore.

Nebulizer assembly 54 here includes a moldable plastic outer body 55 and a moldable plastic central body 56 having a nebulizer orifice 56a and a deflector element 56b (FIGS. 5, 7 and 8). Mounted within the central body portion 56 is an elongated fluid flow tube 60. Fluid flow tube 60 includes a gas inlet port 62 and a gas outlet port 64 that is in communication with nebulizer orifice 56a.

As best seen by referring to FIGS. 8 and 5, nebulizer body 56 is telescopically receivable over flow tube 60 and includes a plurality of circumferentially spaced ribs 68 that cooperate with the outer wall of the flow tube to define a plurality of fluid flow paths 71 (FIG. 5). When the nebulizer body is in position over the flow tube, the components cooperate to define a transverse fluid passageway 74 that is in communication with the plurality of fluid flow passageways 71 and with gas outlet port 64. With this construction, when the reservoir 76 is filled with the aerosolizable liquid medicament "LM" and when the fluid flow tube 60 is interconnected with a source of gas under pressure "S" via a connector tube 77 (FIG. 2), the aerosolizable liquid medicament "LM" will, in a manner presently to be described, be aerosolized to produce a multiplicity of particles of aerosolized medication.

Removably connected to central body portion 60 is a bottom closure assembly 78 that includes a supporting base 80 and an elongated stem 82 that is connected to supporting base 80 in the manner best seen in FIG. 8 of the drawings. As indicated in the drawings, the fluid flow tube is telescopically, sealably receivable within the elongated stem for sealing the gas inlet port 62 thereof. In one form of the invention, supporting base 80 functions to enable proper positioning of nebulizer for automated robotic filling procedures. In this regard, it should be noted that the overall design of the nebulizer unit of the present invention is such that it is fully compatible with an automated robotic assembly process, with automated robotic post-assembly functional testing and quality assurance inspection, and with automatic robotic packaging processes for packaging and shipping the assembled unit in a fashion that meets the needs of the pharmaceutical companies.

As can clearly be seen by referring to FIG. 2, when the nebulizer assembly 54 is interconnected with housing 16, the volume of air surrounding the point of Venturi action "VA" within sub-chamber 44 has been substantially reduced compared to that of the prior art device illustrated in FIG. 1. Additionally, and quite importantly, this point of mist production is located immediately beneath the air flow passageway 85 carrying fluids to the patient and the air flow passageway 87 that communicates with room air via the exit port 34.

In using the device of the invention, when the patient inhales the momentary requirement for air flow to the patient lungs typically far exceeds the 6-8 LPM of gas flow to nebulizer 54. As depicted in FIG. 5, upon patient inhalation air is urged to flow through tubular flow directors 50 along a flow path immediately above the port of entry of aerosol from nebulizer 54 into sub-chamber 44. As this channeled increase in air flow along the edge portions of nebulizer port 32 moves toward the patient, a partial vacuum is created within sub-chamber 44 proximate the area of nebulizer output. This additional partial vacuum, created by the novel baffling assembly 40, is added to that generated by gas flow through the nebulizer thusly markedly increasing the rate of liquid-to-aerosol conversion. With the proper positioning and sizing of air channeling pathways 50 in the baffle assembly, bench studies have shown an increase in rate of aerosol mist production by factors of 200%-300%.

Having now described the invention in detail in accordance with the requirements of the patent statues, those skilled in this art will have no difficulty in making changes and modifications in individual parts or their relative assembly in order to meet specific requirements or conditions. Such changes and modifications may be made without departing from the scope and spirit of the invention, as set forth in the following claims.

I claim:

1. A nebulizer unit for delivering a multiplicity of particles of aerosolized medication to a patient comprising:
    (a) a nebulizer housing having interconnected top, bottom, side and end walls defining a chamber, said bottom wall having a nebulizer port, one of said end walls having an inlet port and the other of said end walls having a particle outlet port in communication with the patient;
    (b) an airflow baffle assembly connected to said top, bottom and side walls, said airflow baffle assembly including an airflow baffle located between said nebulizer port and said inlet port to divide said chamber into first and second sub-chambers, said airflow baffle assembly further including a pair of transversely spaced apart tubular flow directors connected to said airflow baffle and extending into said second sub-chamber, said tubular flow directors providing communication between said first and second sub-chambers; and
    (c) a nebulizer assembly connected to said nebulizer port and in communication with said second sub-chamber for converting aerosolizable liquid medicament into an aerosolized medication and for introducing said aerosolized medication into said second sub-chamber.

2. The nebulizer unit as defined in claim 1 further including a patient mouthpiece connected to said particle outlet port.

3. The nebulizer unit as defined in claim 1 in which said nebulizer assembly comprises a nebulizer body having a first open end, a second end and a nebulizer orifice.

4. A nebulizer unit for delivering a multiplicity of particles of aerosolized medication to a patient comprising:

(a) a nebulizer housing having interconnected top, bottom, side and end walls defining a chamber, said bottom wall having a nebulizer port, one of said end walls having an inlet port and the other of said end walls having a particle outlet port in communication with the patient;
(b) a patient mouthpiece connected to said particle outlet port;
(c) an airflow baffle assembly connected to said top, bottom and side walls, said airflow baffle assembly including an airflow baffle located between said nebulizer port and said inlet port to divide said chamber into first and second sub-chambers, said airflow baffle assembly further including a pair of transversely spaced apart tubular flow directors connected to said airflow baffle and extending into said second sub-chamber, said tubular flow directors providing communication between said first and second sub-chambers; and
(d) a nebulizer assembly connected to said nebulizer port and in communication with said second sub-chamber for converting aerosolizable liquid medicament into an aerosolized medication and for introducing said aerosolized medication into said second sub-chamber, said nebulizer assembly comprising:
  (i) a nebulizer body having a first open end, a second end and a nebulizer orifice; and
  (ii) a fluid flow tube connected to said second end of said nebulizer body, said fluid flow tube having a gas inlet port and a gas outlet port in communication with said nebulizer orifice for aerosolizing said aerosolizable liquid medicament to produce a multiplicity of particles of aerosolized medication.

5. A nebulizer unit for delivering a multiplicity of particles of aerosolized medication to a patient comprising:
(a) a nebulizer housing having a chamber provided with a nebulizer port, an inlet port and a particle outlet port in communication with the patient;
(b) an airflow baffle disposed within said chamber and located between said nebulizer port and said inlet port to divide said chamber into first and second sub-chambers, said airflow baffle having a pair of transversely spaced apart openings for providing communication between said first and second sub-chambers and including a pair of tubular flow directors extending into said second sub-chamber, said tubular flow directors being in communication with said openings in said airflow baffle; and
(c) a nebulizer assembly connected to said nebulizer port and in communication with said second sub-chamber for converting aerosolizable liquid medicament into an aerosolized medication and for introducing said aerosolized medication into said second sub-chamber.

* * * * *